US 6,413,204 B1

(12) United States Patent
Winkler et al.

(10) Patent No.: US 6,413,204 B1
(45) Date of Patent: *Jul. 2, 2002

(54) INTERSTITIAL BRACHYTHERAPY APPARATUS AND METHOD FOR TREATMENT OF PROLIFERATIVE TISSUE DISEASES

(75) Inventors: Rance A. Winkler, Atlanta; Timothy J. Patrick; James Stubbs, both of Alpharetta, all of GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/293,524

(22) Filed: Apr. 15, 1999

Related U.S. Application Data

(63) Continuation-in-part of application No. 08/900,021, filed on Jul. 4, 1997, now Pat. No. 5,913,813.

(51) Int. Cl.$^7$ ................................................ A61N 5/00
(52) U.S. Cl. ........................................................ 600/3
(58) Field of Search ........................................ 600/1–8

(56) References Cited

U.S. PATENT DOCUMENTS

| | | | |
|---|---|---|---|
| 3,324,847 A | 6/1967 | Zoumboulis | 128/1.2 |
| 3,872,856 A | 3/1975 | Clayton | 128/1.2 |
| 4,417,576 A | 11/1983 | Baran | 128/207.15 |
| 4,706,652 A | 11/1987 | Horowitz | 128/1.2 |
| 4,754,745 A | 7/1988 | Horowitz | 128/1.2 |
| 4,763,642 A | 8/1988 | Horowitz | 128/1.2 |

(List continued on next page.)

FOREIGN PATENT DOCUMENTS

| | | | |
|---|---|---|---|
| EP | 0340881 | 11/1989 | ............ A61N/5/10 |
| EP | 0867200 | 9/1998 | |
| GB | 2105201 | 3/1983 | ............ A61N/1/06 |
| WO | 9210932 | 7/1992 | ............ A61N/5/02 |
| WO | 9309724 | 5/1993 | ............ A61B/17/36 |
| WO | 9719723 | 6/1997 | ............ A61N/5/00 |
| WO | 9812979 | 4/1998 | ............ A61B/19/00 |
| WO | 9911325 | 3/1999 | |
| WO | 9933515 | 7/1999 | |
| WO | 9942163 | 9/1999 | |

OTHER PUBLICATIONS

A. Bex et al., *A System for Focal Intracavitary Irradiation of Bladder Cancer with Remote Iridium–192 Afterloading*, 21 Eur Urol 1992, 245–249 (1992).

Ashpole, R.D. et al., "A New Technique of Brachtherapy for Malignant Gliomas with Caesium–137: A New Method Utilizing a Remote Afterloading System," Clinical Oncology, vol. 2, 333–7 (1990).

Chun, M. et al., "Interstitial Iridium–192 Implantation for Malignant Brain Tumours. Part II: Clinical Experience," *The British Journal of Radiology*, vol. 62, 158–62 (1989).

Garfield, J. et al., "Postoperative Intracavitary Chemotherapy of Malignant Gliomas," *J. Neurosurg.*, vol. 39, 315–22 (Sep. 1973).

(List continued on next page.)

*Primary Examiner*—John P. Lacyk
(74) *Attorney, Agent, or Firm*—Thomas J. Engellenner; Ronald E. Cahill; Nutter, McClennen & Fish, LLP

(57) ABSTRACT

An interstitial brachytherapy apparatus for delivering radioactive emissions to an internal body location includes a catheter body member having a proximal end and distal end, an inner spatial volume disposed proximate to the distal end of the catheter body member, an outer spatial volume defined by an expandable surface element disposed proximate to the distal end of the body member in a surrounding relation to the inner spatial volume, and a radiation source disposed in the inner spatial volume.

36 Claims, 3 Drawing Sheets

U.S. PATENT DOCUMENTS

| | | | |
|---|---|---|---|
| 4,821,725 A | 4/1989 | Azam et al. | 128/420 A |
| 4,867,741 A | 9/1989 | Portnoy | 604/10 |
| 5,084,001 A | 1/1992 | Van't Hooft et al. | 600/3 |
| 5,084,015 A | 1/1992 | Moriuchi | 604/96 |
| 5,106,360 A | 4/1992 | Ishiwara et al. | 600/2 |
| 5,112,303 A | 5/1992 | Pudenz et al. | 604/49 |
| 5,152,747 A | 10/1992 | Olivier | 604/93 |
| 5,236,410 A | 8/1993 | Granov et al. | 600/12 |
| 5,429,582 A | 7/1995 | Williams | 600/2 |
| 5,484,384 A | 1/1996 | Fearnot | 600/3 |
| 5,503,613 A | 4/1996 | Weinberger | 600/3 |
| 5,566,221 A | 10/1996 | Smith et al. | 378/145 |
| 5,611,767 A | 3/1997 | Williams | 600/2 |
| 5,662,580 A | 9/1997 | Bradshaw et al. | 600/3 |
| 5,707,332 A | 1/1998 | Weinberger | 600/3 |
| 5,713,828 A | 2/1998 | Coniglione | 600/7 |
| 5,720,717 A | 2/1998 | D'Andrea | 604/21 |
| 5,764,723 A | 6/1998 | Weinberger et al. | 378/65 |
| 5,782,742 A | 7/1998 | Crocker et al. | 600/3 |
| 5,785,688 A | 7/1998 | Joshi et al. | 604/141 |
| 5,913,813 A * | 6/1999 | Williams et al. | 600/3 |
| 5,924,973 A * | 7/1999 | Wenberger | 600/3 |
| 6,036,631 A | 3/2000 | McGrath et al. | 600/3 |
| 6,059,812 A * | 5/2000 | Clerc et al. | 600/3 |

OTHER PUBLICATIONS

Gutin, P. et al., "Brachytherapy of Recurrent Malignant Brain Tumors With Removable High–Activity Iodine–125 Sources," *J. Neurosurg.*, vol. 60, 61–8 (1984).

Johannesen, T.B. et al., "Intracavity Fractionated Balloon Brachytherapy in Gilioblastoma," *Acta Neurochir (Wien)*, vol. 141, 127–33 (1999).

Leibel, S. et al., "The Integration of Interstitial Implantation Into the Preliminary Mangement of Patients With Malignant Gliomas: Results of a Phase II Northern California Oncology Group Trial," *Am. J. Clin. Oncol. (CCT)*, vol. 10, No. 2, p. 106 (1987).*

Roberts, D. et al., "Interstitial Hyperthermia and Iridium Brachytherapy in Treamtnet of Malignant Glioma," *J. Neurosurg.*, vol. 64, 581–7 (1986).*

Wu, A. et al., "Interstitial Iridium–192 Implantation for Malignant Brain Tumours, Part 1: Techniques of Dosimetry Planning," *The British Journal of Radiology*, vol. 62, 154–7 (1989).*

* cited by examiner

DISTANCE FROM SURFACE OF OUTER VOLUME

INTERSTITIAL BRACHYTHERAPY APPARATUS AND METHOD FOR TREATMENT OF PROLIFERATIVE TISSUE DISEASES

CROSS-REFERENCE TO RELATED APPLICATIONS

This application is a continuation-in-part of U.S. patent application Ser. No. 08/900,021, filed Jul. 24, 1997, now U.S. Pat. No. 5,913,813 the contents of which are specifically incorporated herein by reference.

BACKGROUND OF THE INVENTION

The invention relates generally to apparatus for use in treating proliferative tissue disorders, and more particularly to an apparatus for the treatment of such disorders in the body by the application of radiation.

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance or normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

Interstitial brachytherapy is traditionally carried out using radioactive seeds such as $^{125}I$ seeds. These seeds, however, produce inhomogeneous dose distributions. In order to achieve a minimum prescribed dosage throughout a target region of tissue, high activity seeds must be used, resulting in very high doses being delivered in some regions in proximity to the seed or seeds which can cause radionecrosis in healthy tissue.

Williams U.S. Pat. No. 5,429,582, entitled "Tumor Treatment," describes a method and apparatus for treating tissue surrounding a surgically excised tumor with radioactive emissions to kill any cancer cells that may be present in the tissue surrounding the excised tumor. In order to implement the radioactive emissions, Williams provides a catheter having an inflatable balloon at its distal end that defines a distensible reservoir. Following surgical removal of a tumor, the surgeon introduces the balloon catheter into the surgically created pocket left following removal of the tumor. The balloon is then inflated by injecting a fluid having one or more radionuclides into the distensible reservoir via a lumen in the catheter.

The apparatus described in Williams solves some of the problems found when using radioactive seeds for interstitial brachytherapy, but leaves some problems unresolved. The absorbed dose rate at a target point exterior to a radioactive source is inversely proportional to the square of the distance between the radiation source and the target point. As a result, where the radioactive source has sufficient activity to deliver a prescribed dose, say 2 centimeters into the target tissue, the tissue directly adjacent the wall of the distensible reservoir, where the distance to the radioactive source is very small, may still be overly "hot" to the point where healthy tissue necrosis may result. In general, the amount of radiation desired by the physician is a certain minimum amount that is delivered to a region up to about two centimeters away from the wall of the excised tumor. It is desirable to keep the radiation that is delivered to the tissue in the target treatment region within a narrow absorbed dose range to prevent over-exposure to tissue at or near the reservoir wall, while still delivering the minimum prescribed dose at the maximum prescribed distance from the reservoir wall.

There is still a need for an instrument which can be used to deliver radiation from a radioactive source to target tissue within the human body with a desired intensity and at a predetermined distance from the radiation source without over-exposure of body tissues disposed between the radiation source and the target.

SUMMARY OF THE INVENTION

The present invention solves the problems described above by providing an interstitial brachytherapy apparatus for delivering radioactive emissions to an internal body location. The apparatus includes a catheter body member having a proximal end and distal end, an inner spatial volume disposed proximate to the distal end of the catheter body member, an outer spatial volume defined by an expandable surface element disposed proximate to the distal end of the body member in a surrounding relation to the inner spatial volume, and a radiation source disposed in the inner spatial volume. The inner and outer spatial volumes are configured to provide an absorbed dose within a predetermined range throughout a target tissue. The target tissue is located between the outer spatial volume expandable surface and a minimum distance outward from the outer spatial volume expandable surface. The predetermined dose range is defined as being between a minimum prescribed absorbed dose for delivering therapeutic effects to tissue that may include cancer cells, and a maximum prescribed absorbed dose above which healthy tissue necrosis may result.

In different embodiments, the inner spatial volume can be defined by a distensible polymeric wall containing radioactive source material which can be a fluid material, by a solid radioactive source, or by a region containing a plurality of solid radioactive sources. The outer spatial volume is defined by an expandable surface element that may be, for example, an inflatable polymeric wall or an expandable cage. The expandable surface element can cause tissue to conform to its intended shape, and preferably, the apparatus creates absorbed isodose profiles in the target tissue that are substantially similar in shape to the expandable surface element in substantially three dimensions.

The invention also provides a method for treating a proliferating tissue disease using interstitial brachytherapy at an internal body location. The method includes surgically creating access to the proliferating tissue within a patient and surgically resecting at least a portion of the proliferating tissue to create a resection cavity within body tissue. An interstitial brachytherapy apparatus for delivering radioactive emissions as described above is then provided and intra-operatively placed into the resection cavity. After a prescribed absorbed dose has been delivered to tissue surrounding the apparatus, the apparatus is removed. The radioactive source material may be placed into the interstitial brachytherapy apparatus after the apparatus is placed in the resection cavity, and may be removed before the apparatus is removed. The method has particular applications to brain and breast cancers.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
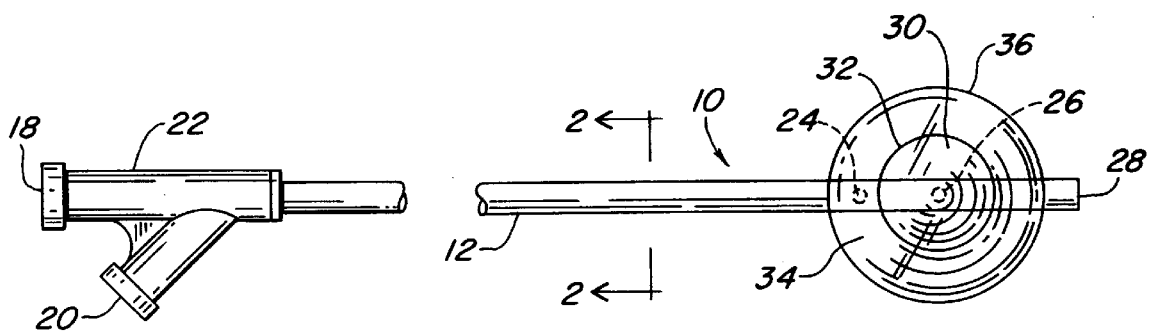
FIG. 1 is a side view of an interstitial brachytherapy apparatus of the invention for delivering radioactive emissions to body tissue.
Figure 2:
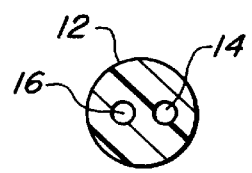
FIG. 2 is a cross-sectional view taken along the line 2—2 in FIG. 1.

A surgical instrument 10 for providing radiation treatment to proliferative tissue in a living patient is illustrated in FIG. 1. Surgical instrument 10 includes a tubular body member 12 having first and second lumens 14 and 16 (FIG. 2) extending from proximal ports 18 and 20 in a molded plastic hub 22 to inflation ports 24 and 26 formed through the side wall of the tube 12 and intersecting with the lumens 14 and 16, respectively.

Affixed to the tubular body 12 proximate the distal end 28 thereof is an inner spatial volume 30 which may be defined by a generally spherical polymeric film wall 32. The interior of the inner volume 30 is in fluid communication with the inflation port 26. Surrounding inner spatial volume 30 is an outer spatial volume 34 defined by an outer polymeric film wall 36 that is appropriately spaced from the wall 32 of the inner spatial volume 30 when the two volumes are inflated or otherwise supported. Outer volume 34 encompasses inflation port 24. With no limitation intended, the distensible polymeric film walls may comprise a biocompatible, radiation resistant polymer, such as silastic rubbers, polyurethanes, polyethylene, polypropylene, polyester, or PVC.

The embodiment of FIG. 1 includes inner and outer spatial volumes 30 and 34, one inside the other. The outer spatial volume 34, being the volume defined by the space between the inner spherical wall 32 and the outer spherical wall 36, may be filled with air or, alternatively, a radiation absorbing fluid, such as a contrast media used in angiography. The inner volume 30 is then filled with a material containing a predetermined radionuclide, for example, I-125, I-131, Yb-169 or other source of radiation, such as radionuclides that emit photons, beta particles, gamma radiation, or other therapeutic rays. The radioactive material contained within the inner chamber 32 can be a fluid made from any solution of radionuclide(s), e.g., a solution of I-125 or I-131. A radioactive fluid can also be produced using a slurry of a suitable fluid containing small particles of solid radionuclides, such as Au-198, Y-90. Moreover, the radionuclide(s) can be embodied in a gel. One radioactive material useful in the invention is Iotrex™, a sterile single use, non-pyrogenic solution containing sodium 3-($^{125}$I)iodo-4-hydroxybenzenesulfonate ($^{125}$I-HBS), available from Proxima Therapuetics, Inc. of Alpharetta, Ga.

As an alternative method of providing radioactive source material, such material may be coated on, chemically bonded to, or copolymerized with the material forming inner spherical wall 32.

Where the radioactive source material is provided as a fluid or gel within inner spherical wall 32, it may be desirable to provide a solid outer spherical wall 36. Should inner spherical wall 32 rupture, the radioactive source material will be retained within outer spherical wall 36 and will not leak into the patient. For further safety, the burst strength of inner spherical wall 32 may be designed so as to be lower than that of outer spherical wall 36. In this way, inner spherical wall 32 will rupture under stress first, releasing its contents into the larger combined space of the inner and outer volumes 30, 34 and releasing any pressure built up within the inner spherical wall 32 and reducing the risk that radioactive material will spill into the patient. In the event of such a rupture, radioactive fluid could be drained from the apparatus through port 24 by way of lumen 14, and also from port 26 by way of lumen 16.

Figure 3:
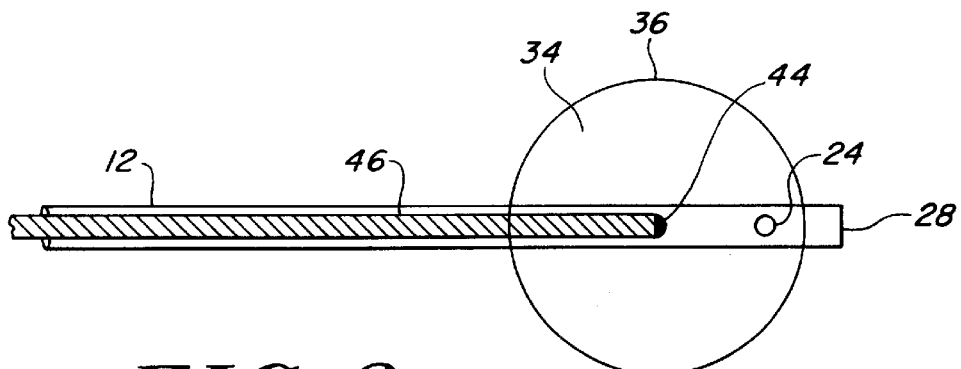
FIG. 3 is an additional embodiment of an interstitial brachytherapy apparatus of the invention having a solid radiation source.

In a further embodiment, illustrated in FIG. 3, instead of having the inner spatial volume 30 defined by a generally spherical polymeric film wall as at 32, the catheter body member 12 may have a solid spherical radiation emitting material 44 as the inner spatial volume 30. For example, radioactive micro spheres of the type available from the 3M Company of St. Paul, Minn., may be used. This radioactive source can either be preloaded into the catheter at the time of manufacture or loaded into the device after it has been implanted into the space formerly occupied by the excised tumor. The solid radiation emitting material 44 can be inserted through catheter 12 on a wire 46, for example, using an afterloader (not shown). Such a solid radioactive core configuration offers an advantage in that it allows a wider range of radionuclides than if one is limited to liquids. Solid radionuclides that could be used with the delivery device of the present invention are currently generally available as brachytherapy radiation sources. In this embodiment solid spherical inner spatial volume 30 is surrounded by outer spherical wall 36, defining outer spatial volume 34 between the outer spherical wall 36 and the inner spatial volume 30 with the outer spatial volume 34 occupied by a radioactive ray absorbent material, such as air, water or a contrast material.

Figure 4:
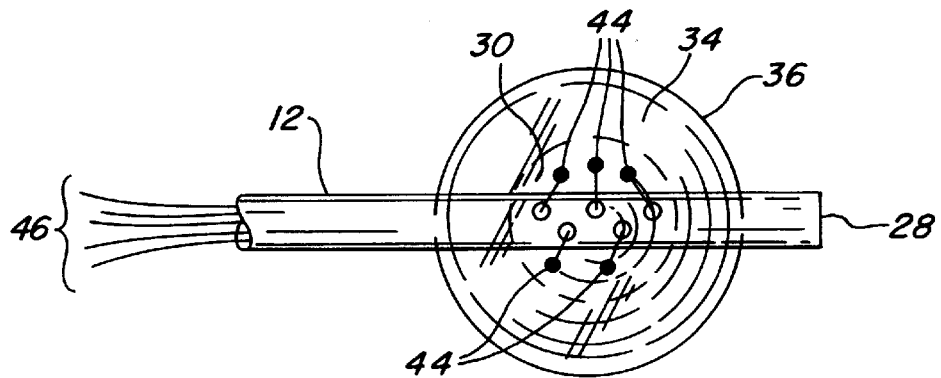
FIG. 4 is an additional embodiment of an interstitial brachytherapy apparatus of the invention having a radiation source comprising a plurality of solid radiation particles.

In a further embodiment, illustrated in FIG. 4, inner spatial volume 30, instead of comprising a single solid sphere, may comprise a plurality of radiation emitting particles 44 strategically placed within the inner spatial volume 30 so as to radiate in all directions with a substantially equal intensity. This plurality of radiation emitting particles 44 can be mounted on the distal ends of a plurality of wires 46 that are routed through the catheter body 12 and exit a plurality of ports formed through the wall of the catheter body and reaching the lumen. This arrangement allows the exact positioning of the individual radiation sources 44 to be positioned so as to generate a desired resultant profile.

Figure 5:
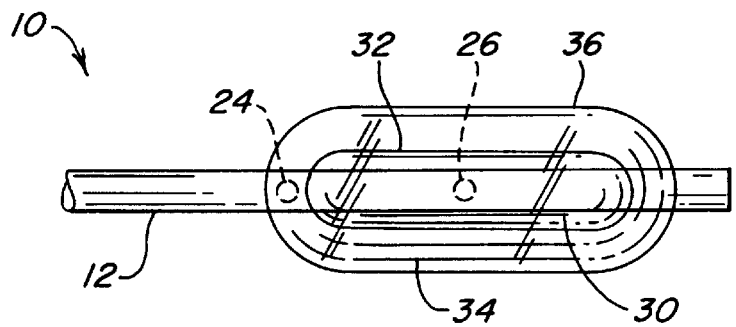
FIG. 5 depicts a further embodiment of the invention wherein the inner and outer spatial volumes of the interstitial brachytherapy apparatus are non-spherical.

As illustrated in FIG. 5, it is not essential to the invention that the volumes 30 and 34 have spherical walls, so long as the resultant dosing profile is consistent with the shape of the outer volume 34. That is, the absorbed dose within the target tissue at points equidistant from the surface 36 of the outer spatial volume 34 should be substantially uniform in substantially every direction. Put another way, the three dimensional isodose profiles generated by the radiation source should be substantially similar in shape to the outer spatial volume 34. Where the inner and outer spatial volumes are created by inflatable membranes and one of the volumes contains a fluid radiation source, this can be achieved by ensuring that the spacing between the wall of the inner volume and the wall of the outer volume remain generally constant. In either the concentric spherical embodiment of FIG. 1 or the non-spherical configuration of FIG. 5, this result can be achieved by careful placement of precision blown or molded polymer partitions or by using compressible foams or mechanical spacers in the form of webs joining the inner wall 32 to the outer wall 36. The desired isodose profiles conforming to the shape of the outer spatial volume 34 can also be obtained, for example, by strategic placement of a plurality of radioactive particle sources within the inner spatial volume 30. Where the apparatus of the invention is deployed in soft tissue, it may also be important for the surface 36 of the outer spatial volume 34 to be sufficiently firm so as to force the target tissue to take on the shape of the surface 36 so that the desired relationship between the isodose profiles and the target tissue is achieved.

Figure 6:
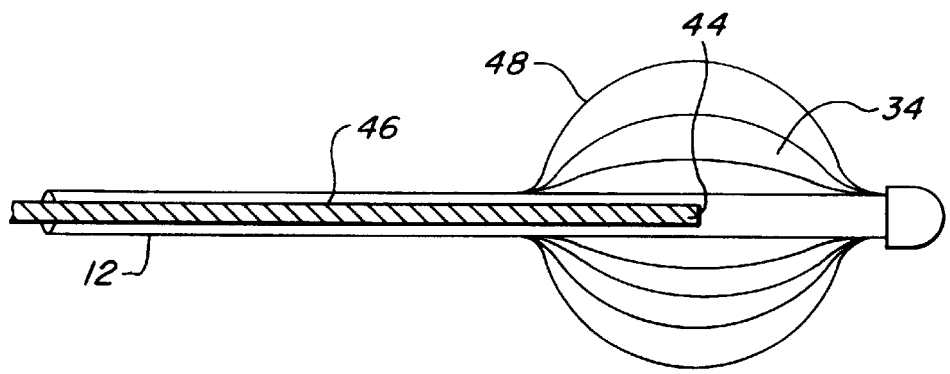
FIG. 6 illustrates an interstitial brachytherapy apparatus of the invention having an expandable outer spatial volume surface.

When used in an interstitial application, the surface of the outer spatial volume 34 must establish a relationship between the inner spatial volume 30 and the target tissue so as to achieve the aforementioned isodose profile, however, the surface of the outer volume need not be a solid material. For example, as illustrated in FIG. 6, the surface of the outer volume 34 could be an expandable cage 48 formed from a shape memory metal, such as nitinol, or a suitable plastic, such as an expandable polyethylene cage. Such a cage can be formed in the desired shape to conform to a particular isodose profile, then be contracted for delivery to the target site in vivo, then expanded to cause the tissue surrounding the surgically resected region to take the appropriate shape. The size of the outer spatial volume 34 generally will correspond approximately to the amount of tissue resected, or be slightly larger, allowing the expandable surface of the outer spatial volume to urge tissue on the surface of the resected region into the appropriate shape to promote an even dose distribution around the outer spatial volume in the target tissue. In typical applications, the outer spatial volume has a diameter of approximately 2 to 4 centimeters. In these same applications, where the radiation source is provided as a fluid within an inner balloon, the inner balloon generally has a diameter of approximately 0.5 to 3 centimeters.

Figure 7A:
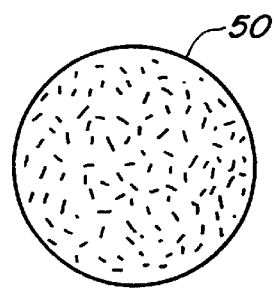
FIGS. 7A–D illustrate the absorbed dose versus distance into target tissue for several interstitial brachytherapy apparatus configurations.
Figure 7B:
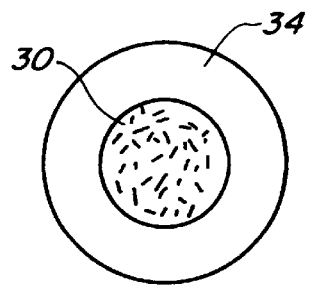
Figure 7C:
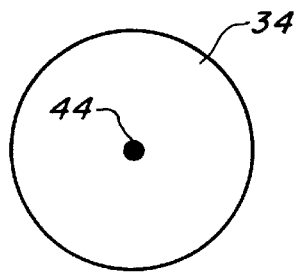

FIGS. 7A–D illustrate the ability of an interstitial brachytherapy apparatus of the invention to deliver a minimum prescribed dose within target tissue while avoiding necrosis inducing radiation "hot spots" in tissue proximate to the apparatus. FIG. 7A illustrates an interstitial brachytherapy apparatus (device A) such as those employed in U.S. Pat. No. 5,429,582, having a single spatial volume 50 filled with a radioactive material in solution. FIG. 7B illustrates an interstitial brachytherapy apparatus (device B) of the invention having a first, inner spatial volume 30 filled with a radioactive material in solution and defined by membrane 32, and a second, outer spatial volume 34 defined by membrane 36 that is substantially evenly spaced apart from membrane 32 in substantially three dimensions. FIG. 7C illustrates an additional interstitial brachytherapy apparatus (device C) of the invention having a solid, spherical radiation source 44 as the inner spatial volume and a spherical outer spatial volume 34 defined by membrane 36.

Figure 7D:
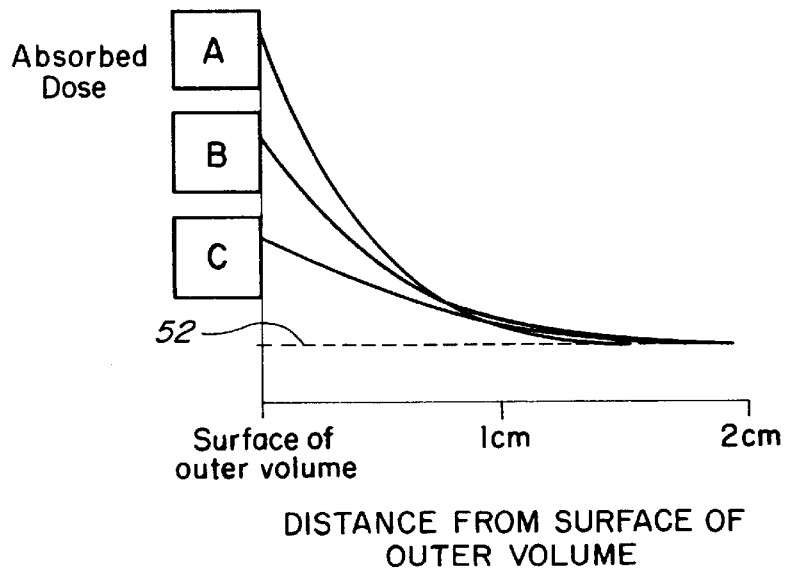

Each of the devices illustrated in FIGS. 7A–C can be configured to deliver a substantially uniform dose at a given distance into the target tissue from the surface of the outer spatial volume 34 (or from single spatial volume 50 for device A) and to deliver a minimum prescribed dose within a given prescribed depth range into the tissue from the surface of the outer spatial volume 34. However, the different devices provide very different dose profiles as a function of distance from the surface of the outer volume as illustrated in FIG. 7D. FIG. 7D plots the absorbed dose at a given distance into the target tissue from the surface of the outer spatial volume 34 for each of the devices A, B, and C.

Each device can deliver a minimum prescribed dose 52 at a given distance from the surface of the outer spatial volume. For example, device A can readily be configured to provide a dose in a therapeutic range, say between 40 to 60 Gray, at a distance between 0.5 and 1.0 cm from the outer spatial volume for an outer spatial volume having a diameter of 4.0 cm and being in contact with the resection cavity wall. In a typical embodiment, the radioactive source material ranges from approximately 150 to 450 mCi in activity and encompasses most of the target treatment area with a 0.4 to 0.6 Gray/hour isodose contour. At this treatment rate, treatment may be completed in approximately 3 to 7 days, or more commonly, in approximately 3 to 5 days.

In order to reach the minimum prescribed dosage at this distance, however, device A must provide a dose proximate to the surface of the outer spatial volume that is substantially larger than the minimum prescribed dose. For the 4.0 cm diameter outer spatial volume example, the absorbed dosage would be approximately 131 Gray at the outer spatial volume surface. Ideally, radiation therapy should make use the inherent difference in radiosensitivity between the tumor and the adjacent normal tissues to destroy cancerous tissue while causing minimal disruption to surrounding normal tissues. At high doses of radiation, however, the percentage of exposed cells that survive treatment decreases with first-order kinetics in proportion to increasing radiation dose. With increasing cell death comes increasing risk of necrosis or tissue death in healthy tissue that is treated with a high dose of radiation. Accordingly, it is desirable to keep the maximum radiation dose delivered by the brachytherapy apparatus as low as possible while still delivering the desired therapeutic dose to the desired range of tissue.

Comparing the plots A, B, and C, the absorbed dose profile in the space between the 2 cm site and the surface of the outer spatial volume for the devices of the invention is maintained in a much narrower range, preventing overtreatment of body tissue at or close to the surface of the outer volume of the device. Because devices B and C provide an outer spatial volume 34 between the radioactive source and the target tissue, these devices can use hotter radiation sources to reach the minimum prescribed dosage, but take advantage of the distance between the radioactive source and the target tissue provided by the outer spatial volume 34 to reduce or eliminate hot spots in the target tissue.

Returning to the 4.0 cm diameter outer spatial volume example, if the radiation source is contained within an inner spatial volume, say a solid radioactive sphere such as device C, the absorbed dose profile becomes much different. If the radiation source is configured to provide the same 60 Gray dose at 0.5 cm into the target tissue, the absorbed dose at the outer spatial volume surface is only 94 Gray—a significant decrease from the 131 Gray dose for a type A device. In addition, the treatment range for the type C device will be extended under these circumstance as compared to the type A device, delivering a 40 Gray dose beyond 1.0 cm into the target tissue and delivering approximately double the dose at 3.0 cm into the target tissue. In one embodiment, the inner and outer spatial volumes are configured to control the absorbed dose at the outer spatial volume surface so that the absorbed dose is no greater than about 100 Gray while providing a therapeutic absorbed dose into the target tissue at the desired range. The capability of the apparatus of the invention to deliver absorbed doses deeper into the target tissue than prior interstitial brachytherapy devices while controlling the dose in proximity to the apparatus to reduce or eliminate the risk of healthy tissue necrosis allows for the use of brachytherapy in a greater number of cases.

The interstitial brachytherapy apparatus of the invention can be used in the treatment of a variety of malignant tumors, and is especially useful for in the treatment of brain and breast tumors.

Many breast cancer patients are candidates for breast conservation surgery, also known as lumpectomy, a procedure that is generally performed on early stage, smaller tumors. Breast conservation surgery is typically followed by postoperative radiation therapy. Studies report that 80% of breast cancer recurrences after conservation surgery occur near the original tumor site, strongly suggesting that a tumor bed "boost" of local radiation to administer a strong direct dose may be effective in killing any remaining cancer and preventing recurrence at the original site. Numerous studies and clinical trials have established equivalence of survival for appropriate patients treated with conservation surgery plus radiation therapy compared to mastectomy.

Surgery and radiation therapy are the standard treatments for malignant solid brain tumors. The goal of surgery is to remove as much of the tumor as possible without damaging vital brain tissue. The ability to remove the entire malignant tumor is limited by its tendency to infiltrate adjacent normal tissue. Partial removal reduces the amount of tumor to be treated by radiation therapy and, under some circumstances, helps to relieve symptoms by reducing pressure on the brain.

A method according to the invention for treating these and other malignancies begins by surgical resection of a tumor site to remove at least a portion of the cancerous tumor and create a resection cavity. Following tumor resection, but prior to closing the surgical site, the surgeon intraoperatively places an interstitial brachytherapy catheter apparatus, having an inner spatial volume and an outer spatial volume as described above but without having the radioactive source material loaded, into the tumor resection cavity. Once the patient has sufficiently recovered from the surgery, the interstitial brachytherapy catheter is loaded with a radiation source. The radioactive source dwells in the catheter until the prescribed dose of radiotherapy is delivered, typically for approximately a week or less. The radiation source is then retrieved and the catheter is removed. The radiation treatment may end upon removal of the brachytherapy apparatus, or the brachytherapy may be supplemented by further doses of radiation supplied externally.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An interstitial brachytherapy apparatus for delivering radioactive emissions to an internal body location comprising:

(a) a catheter body member having a proximal end and distal end;

(b) an inner spatial volume disposed proximate to the distal end of the catheter body member;

(c) an outer spatial volume defined by an expandable surface element disposed proximate to the distal end of the body member in a surrounding relation to the inner spatial volume; and (d) a radiation source disposed in the inner spatial volume and generating a three-dimensional isodose profile that is substantially similar in shape to the expandable surface element.

2. The apparatus of claim 1, wherein the inner and outer spatial volumes are configured to provide a minimum prescribed absorbed dose for delivering therapeutic effects to a target tissue, the target tissue being defined between the outer spatial volume expandable surface and a minimum distance outward from the outer spatial volume expandable surface, the apparatus providing a controlled dose at the outer spatial volume expandable surface to reduce or prevent necrosis in healthy tissue proximate to the expandable surface.

3. The apparatus of claim 2, wherein a predetermined spacing is provided between said inner spatial volume and the expandable surface element.

4. The apparatus of claim 3, wherein the expandable surface element is adapted to contact tissue surrounding a resected cavity and adapted to conform the tissue to the desired shape of the expandable surface element.

5. The apparatus of claim 2, wherein the minimum prescribed absorbed dose is 40 Gray at a distance of at least one centimeter from the expandable surface element.

6. The apparatus of claim 5, wherein the dose rate in at least a portion of the target tissue is between about 0.4 and 0.6 Gray/hour.

7. The apparatus of claim 5, wherein the maximum absorbed dose delivered to the target tissue is less than 100 Gray.

8. The apparatus of claim 2, wherein the outer spatial volume has a diameter between about two and four centimeters.

9. The apparatus of claim 2, wherein the inner spatial volume is an inner closed, distensible chamber defined by a further radiation transparent wall.

10. The apparatus of claim 9, wherein the radioactive source is in a fluid form.

11. The apparatus of claim 10, wherein the expandable surface element is a solid distensible surface and the outer spatial volume is a closed, distensible chamber and the expandable surface element is a radiation transparent wall.

12. The apparatus of claim 11, wherein a burst strength of the distensible chamber defining the outer spatial volume is greater than a burst strength of the chamber defining the inner spatial volume.

13. The apparatus of claim 1, wherein the expandable surface element is an expandable cage.

14. The apparatus of claim 13, wherein the expandable cage comprises a shape memory material.

15. The apparatus of claim 14, wherein the expandable cage comprises nitinol.

16. The apparatus of claim 1, wherein the radiation source is a solid radiation source.

17. The apparatus of claim 1, wherein the radiation source is a plurality of solid radiation sources arranged to provide an isodose profile having a shape substantially similar to the shape of the outer spatial volume.

18. The apparatus of claim 2, wherein the prescribed absorbed dose is delivered to the target tissue in substantially three dimensions.

19. A method for treating a proliferating tissue disease using interstitial brachytherapy at an internal body location comprising:
   (a) surgically creating access to the proliferating tissue in a patient;
   (b) surgically resecting at least a portion of the proliferating tissue to create a resection cavity within body tissue;
   (c) providing an interstitial brachytherapy apparatus for delivering radioactive emissions comprising:
      (i) a catheter body member having a proximal end and distal end;
      (ii) an inner spatial volume disposed proximate to the distal end of the catheter body member;
      (iii) an outer spatial volume defined by an expandable surface element disposed proximate to the distal end of the body member in a surrounding relation to the inner spatial volume; and
      (iv) a radiation source disposed in the inner spatial volume and generating a three-dimensional isodose profile that is substantially similar in shape to the expandable surface element;
   (d) intraoperatively placing the interstitial brachytherapy apparatus into the resection cavity until a prescribed absorbed dose has been delivered to tissue surrounding the apparatus; and
   (e) removing the interstitial brachytherapy apparatus.

20. The method of claim 19, further including placing the radioactive source into the interstitial brachytherapy apparatus after the step of placing the apparatus into the tumor resection cavity.

21. The method of claim 19, further including removing the radioactive source from the interstitial brachytherapy apparatus before the step of removing the apparatus.

22. The method of claim 19, wherein the proliferating tissue is a patient's brain.

23. The method of claim 19, wherein the proliferating tissue is a patient's breast.

24. The method of claim 19, further including configuring the inner and outer spatial volumes to provide a minimum prescribed absorbed dose for delivering therapeutic effects to a target tissue, the target tissue being defined between the outer spatial volume expandable surface and a minimum distance outward from the outer spatial volume expandable surface, the apparatus providing a controlled dose at the outer spatial volume expandable surface to reduce or prevent necrosis in healthy tissue proximate to the expandable surface.

25. The method of claim 24, further including providing a predetermined spacing between said inner spatial volume and the expandable surface element.

26. The method of claim 25, wherein the expandable surface element is adapted to contact tissue surrounding a resected cavity and adapted to conform the tissue to the desired shape of the expandable surface element.

27. The method of claim 24, wherein the minimum prescribed absorbed dose is 40 Gray at a distance of at least one centimeter from the expandable surface element.

28. The method of claim 27, wherein the dose rate in at least a portion of the target tissue is between about 0.4 and 0.6 Gray/hour.

29. The method of claim 27, wherein the maximum absorbed dose delivered to the target tissue is less than 100 Gray.

30. The method of claim 24, wherein the outer spatial volume has a diameter between about two and four centimeters.

31. The method of claim 24, wherein the step of configuring the inner and outer spatial volumes includes expanding the inner and outer spatial volumes.

32. A method for treating a proliferating tissue disease using interstitial brachytherapy at an internal body location comprising:
   (a) surgically creating access to the proliferating tissue in a patient;
   (b) surgically resecting at least a portion of the proliferating tissue to create a resection cavity within body tissue;
   (c) providing an interstitial brachytherapy apparatus for delivering radioactive emissions comprising:
      (i) a catheter body member having a proximal end and distal end;
      (ii) an inner spatial volume disposed proximate to the distal end of the catheter body member;
      (iii) an outer spatial volume defined by an expandable surface element disposed proximate to the distal end of the body member in a surrounding relation to the inner spatial volume; and
      (iv) a radiation source disposed in the inner spatial volume;
   (d) intraoperatively placing the interstitial brachytherapy apparatus into the resection cavity;
   (e) configuring the inner and outer spatial volumes to provide a minimum prescribed absorbed dose for delivering therapeutic effects to a target tissue, the target tissue being defined between the outer spatial volume expandable surface and a minimum distance outward from the outer spatial volume expandable surface, the apparatus providing a controlled dose at the outer spatial volume expandable surface to reduce or prevent necrosis in healthy tissue proximate to the expandable surface; and
   (f) removing the interstitial brachytherapy apparatus.

33. The method of claim 32, wherein the step of configuring the inner and outer spatial volumes includes expanding the inner and outer spatial volumes.

34. A method for treating a proliferating tissue disease using interstitial brachytherapy at an internal body location comprising:
   (a) surgically creating access to the proliferating tissue in a patient;
   (b) surgically resecting at least a portion of the proliferating tissue to create a resection cavity within body tissue;

(c) providing an interstitial brachytherapy apparatus for delivering radioactive emissions comprising:
  (i) a catheter body member having a proximal end and distal end;
  (ii) an inner spatial volume disposed proximate to the distal end of the catheter body member;
  (iii) an outer spatial volume defined by an expandable surface element disposed proximate to the distal end of the body member in a surrounding relation to the inner spatial volume; and
  (iv) a radiation source disposed in the inner spatial volume;
(d) intraoperatively placing the interstitial brachytherapy apparatus into the resection cavity;
(e) adapting the expandable surface element to contact tissue surrounding the resection cavity to conform the tissue to the desired shape of the expandable surface element;
(f) delivering a prescribed absorbed dose to tissue surrounding the apparatus; and
(g) removing the interstitial brachytherapy apparatus.

35. The method of claim 34, wherein the step of adapting the expandable surface element includes expanding the outer surface volume.

36. An interstitial brachytherapy apparatus for delivering radioactive emissions to an internal body location comprising:
  (a) a catheter body member having a proximal end and distal end;
  (b) an inner spatial volume disposed proximate to the distal end of the catheter body member;
  (c) an outer spatial volume defined by an expandable surface element disposed proximate to the distal end of the body member in a surrounding relation to the inner spatial volume; and
  (d) a radiation source disposed in the inner spatial volume;
wherein the inner and outer spatial volumes are configured to provide a minimum prescribed absorbed dose for delivering therapeutic effects to a target tissue, the target tissue being defined between the outer spatial volume expandable surface and a minimum distance outward from the outer spatial volume expandable surface, the apparatus providing a controlled dose at the outer spatial volume expandable surface to reduce or prevent necrosis in healthy tissue proximate to the expandable surface.

* * * * *